(12) United States Patent
Arai et al.

(10) Patent No.: US 7,022,285 B2
(45) Date of Patent: Apr. 4, 2006

(54) INTEGRAL-MULTILAYER ANALYTICAL ELEMENT FOR ANALYSIS OF AMMONIA OR AMMONIA-PRODUCING SUBSTANCE

(75) Inventors: Takaki Arai, Saitama (JP); Fuminori Arai, Saitama (JP); Keiichi Ishizaki, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 200 days.

(21) Appl. No.: 09/978,109

(22) Filed: Oct. 15, 2001

(65) Prior Publication Data

US 2002/0068364 A1   Jun. 6, 2002

(30) Foreign Application Priority Data

Oct. 16, 2000   (JP) .............................. 2000-314757

(51) Int. Cl.
*G01N 31/00*   (2006.01)

(52) U.S. Cl. ............................ 422/56; 422/55; 422/57; 422/83; 422/86; 422/87

(58) Field of Classification Search ................. 422/55, 422/56, 57, 60, 83, 85, 86, 88, 87
See application file for complete search history.

(56) References Cited

U.S. PATENT DOCUMENTS

| | | | | |
|---|---|---|---|---|
| 5,008,078 A | * | 4/1991 | Yaginuma et al. | ............ 422/56 |
| 5,198,335 A | * | 3/1993 | Sekikawa et al. | ............... 435/4 |
| 5,286,624 A | * | 2/1994 | Terashima et al. | ............ 435/12 |
| 6,395,325 B1 | * | 5/2002 | Hedge et al. | .............. 427/2.11 |

* cited by examiner

*Primary Examiner*—Jill Warden
*Assistant Examiner*—Sam P. Siefke
(74) *Attorney, Agent, or Firm*—Reed Smith LLP

(57) ABSTRACT

An integral multilayer analytical element for analysis of ammonia or ammonia-producing substance is provided, which comprises a thin liquid blocking layer having a comparative facility with a thicker liquid blocking layer and is stably fabricated on a common production line employed for different type of slides.

In the integral multilayer analytical element for analysis of ammonia or ammonia-producing substance comprising a transparent support, an indicator layer containing an indicator which produces a detectable change by gaseous ammonia, a liquid blocking layer permitting a gaseous ammonia to pass through, a reagent layer containing an alkaline buffering agent and optionally a reagent capable of reacting with said ammonia-producing substance to produce ammonia, and a spreading layer, adhesively laminated in this order, the improvement which comprises that said liquid blocking layer is composed of at least two porous membranes.

5 Claims, No Drawings ically about 80 to 300 μm.

INTEGRAL-MULTILAYER ANALYTICAL ELEMENT FOR ANALYSIS OF AMMONIA OR AMMONIA-PRODUCING SUBSTANCE

CROSS-REFERENCES TO RELATED APPLICATIONS

This application claims priority of Japanese Application No. 314757/2000 filed Oct. 16, 2000, the complete disclosure of which is hereby incorporated by reference.

FIELD OF THE INVENTION

The present invention relates to an integral multilayer analytical element for use in the analysis of ammonia or an ammonia-producing substance in liquid samples, and more particularly to an integral multilayer analytical element suitable for use in the analysis (assay) of ammonia or an ammonia-producing substance, such as creatinine, urea, etc., in body fluids, such as blood, urine, etc.

BACKGROUND OF THE INVENTION

Up to now, a variety of the so-called dry chemistry methods have been proposed in order to carry out the analysis of urea nitrogen in body fluids simply and rapidly without personal errors. A typical dry chemistry method uses an integral multilayer analytical element comprising a reagent layer containing urease and an alkaline buffering agent, an indicator layer for the detection of gaseous ammonia, and a selective permeation layer which is interposed between the reagent and the indicator layers and which permits only gaseous ammonia to pass therethrough.

For example, JP 1977-003488 A (Corresponding to U.S. Pat. No. Re. 30,267) discloses an integral analytical element having the fundamental multilayer structure described above. This analytical element uses a thin hydrophobic polymer layer as a selective permeation layer for gaseous ammonia.

JP 1983-077661 A discloses an integral multilayer analytical element for use in the analysis of ammonia or an ammonia-producing substance in liquid samples comprising a laminate of a transparent support, an indicator layer for gaseous ammonia, a liquid blocking layer, a reaction layer containing an alkaline buffering agent and a optionally reagent capable of producing ammonia by the reaction with the ammonia-producing substance, and a porous spreading layer in this order. The integral multilayer analytical element is characterized in that the liquid blocking layer is made of a porous substance comprising pores which function as air vents substantially cutting off liquid samples and permitting gaseous ammonia to pass therethrough under a condition of usage. In the multilayer analytical element, a membrane filter is used as a selectively transmissive layer to approve adhesion to the indicator layer and to give high sensitivity.

Further, JP 1992-157363 A discloses usage of polyvinyl alkyl ether etc. substantially free from ammonia and ammonium ion as an under coating on a support or a binder for an indicator layer to obtain an integral multilayer analytical element for use in the analysis of ammonia or an ammonia-producing substance in liquid samples with higher color development optical density, low color development optical density of background and higher measurement accuracy. JP 1992-157364 A discloses usage of a porous spreading layer containing poly-N-vinyl pyrrolidone and a binder for a reagent layer for an ammonia-producing reaction which does not contain substantially any ammonia, and does not generate ammonia or vary in its binder performance at a pH value of about 9 or more to obtain an integral multilayer analytical element for use in the analysis of ammonia or an ammonia-producing substance in liquid samples with higher color development optical density, low color development optical density of background and higher measurement accuracy.

Yet, the whole thickness of these conventional analytical slides is large since they have a thick porous membrane as a liquid blocking layer. Difference in thickness of these slides and other slides to analyze other analytes requiring no liquid blocking layer is so large that it is unstable to fabricate them on a same production line. However there is a limit in using a thinner porous membrane because of deterioration in its performance as a liquid blocker. Further, though there is a slide having a very thin liquid blocking layer using cellulose acetate butylate, an organic solvent is required to fabricate it, resulting in problems on equipments and environments.

SUMMARY OF THE INVENTION

The purpose of this invention is to provide an integral multilayer analytical element for use in the analysis of ammonia or an ammonia-producing substance comprising a thinner liquid blocking layer retaining a barrier performance same as that of a conventional thicker liquid blocking layer, resulting in a stable fabrication on the same line used to fabricate other type of analytical elements.

The purpose of the invention has been accomplished by means of an integral multilayer analytical element for use in the analysis of ammonia or an ammonia-producing substance in liquid samples comprising a transparent support, an indicator layer containing an indicator which produces a detectable change by reaction with gaseous ammonia, a gaseous ammonia-permeable liquid blocking layer, a reagent layer containing an alkaline buffering agent and optionally a reagent capable of reacting with said ammonia-producing substance to produce ammonia, and a spreading layer laminated in this order, characterized in that the liquid blocking layer is composed of at least two porous membranes.

In the analytical element in accordance with the invention, diameter of pores in the uppermost porous membrane composing the liquid blocking layer, which contacts the reagent layer, is equal to or smaller than that in the second porous membrane from the top. Thus, though the whole thickness of the liquid blocking layer is rather small, liquid blocking properties of the layer can be still maintained. Further, the sensitivity of the analytical element can be also maintained by keeping diameter of pores in the second porous membrane large or by changing material of the second membrane, in spite of small diameter of pores in the uppermost porous membrane.

DESCRIPTION OF THE PREFERED EMBODYMENT

As a support of the analytical element in accordance with the invention, hydrophobic transparent supports which are generally used in such analytical elements and are made of polymers, such as polyethylene terephthalate, polycarbonate and polyvinyl compounds may be used. Thickness of the support is in a range of abut 50 to 1000 μm, typically about 80 to 300 μm.

On the support, an indicator layer is provided. The indicator layer contains one or more compounds which change in absorption wavelength as a result of the reaction with gaseous ammonia (hereinafter, the compound is referred to as a dye precursor). The dye precursor which may be used in the analytical element of this invention includes leuco dyes, such as leucocyanine dye, nitro-substituted leuco dye and leucophthalein dye described in U.S. Pat. No. Re.

30,267, pH indicators, such as Bromophenol Blue, Bromocresol Green, Bromothymol Blue, Qinoline Blue and rosolic acid (see "Kagaku Dai-Jiten" (Chemical Dictionary) Kyoritsu, vol. 10, 63–65), triarylmethane dye precursors, leucobenzilidene pigments (see JP 1982-145273 A), diazonium salts and azo dye couplers, base bleachable dyes, and the like.

At least one dye precursor mentioned above is mixed with water soluble or an organic solvent soluble binder polymer and coated on the transparent support, then dried to provide the indicator layer. Binder polymers for this purpose include polyvinyl alkyl ethers, such as polyvinyl methyl ether, polyvinyl ethyl ether and polyvinyl isobutyl ether, gelatins, such as acid-processed gelatin, alkali-processed gelatin and de-ionized gelatin, cellulose esters, such as cellulose acetate, cellulose acetate butyrate and cellulose acetate propionate, alkyl celluloses, such as methyl cellulose, ethyl cellulose and propyl cellulose, synthetic vinyl polymers, such as polymethylmethacrylate, polyacrylate, polystyrene, polyacrylonitril, polyvinylacetate, polyvinylbutyral, chlorinated polyvinylacetate, polyacrylamide, polyvinylpyrrolidone, polyvinylalcohol and copolymers thereof.

The dye precursor may be used in a range of about 0.1 to 50%, preferably about 0.5 to 20%, based on the weight of the binder. In order to adjust the sensitivity, various buffering agents, organic or inorganic acids may be used to control the pH. The buffering agent may be selected from those mentioned later. As to organic or inorganic acids, ethanesulfonic, asparaginic, azelaic, glutaric, succinic, glutaconic, tartaric, pimelic, malonic, malic, 3,3-dimethyl glutaric, citric, p-toluenesulfonic, perchloric, hydrochloric acid, and the like may be used. In addition, alkalis, such as sodium hydroxide, potassium hydroxide, sodium carbonate, sodium bicarbonate, and the like may be added to the indicator layer. Organic solvents, such as acetone, 2-methoxy ethanol, methyl ethyl ketone, methanol and ethanol, water or mixtures of them may be preferably used to prepare the coating solution for the indicator layer. The coating solution contains solid ingredients such as the dye precursor, binder polymer etc. in a solid concentration of 1 to 30%, preferably 3 to 20%, by weight to prepare the coating solution. The coating solution is coated on the transparent support and dried to form the indicator layer having a dry thickness in a range of about 1 to 30 µm, preferably about 2 to 20 µm.

On the indicator layer, a liquid blocking layer is provided. The liquid blocking layer is composed of a microporous substance having pierced voids which are substantially impermeable to liquids, such as a coating solution, a sample solution etc. and interfering ingredients (e.g. alkaline ingredients) dissolved in these liquids and permeable to gaseous ammonia during fabrication and/or analytical operation of the multilayer analytical element.

The liquid blocking layer in accordance with the present invention is composed of at least two porous membranes, and is characterized in that the diameter of pores in the uppermost porous membrane, which contacts the reagent layer, is equal to or smaller than that in the porous membrane just underlying the uppermost porous membrane. Specifically the diameter of pores in the uppermost membrane is in a range of about 0.01 to 1 µm, preferably 0.04 to 0.2 µm, and the diameter of pores in the membrane just underlying the uppermost membrane is in a range of about 0.2 to 20 µm, preferably about 0.5 to 10 µm. In addition, the former: the latter ratio is in a range of 0.001 to 1.0, preferably 0.01 to 0.5. And now, the diameter of pores in this specification means the average diameter of pores, provided that there is no other particular description.

There is no particular restriction on material of the porous membrane. Polyethylene, polypropylene, fluorine containing polymers such as polytetrafluoroethylene etc., cellulose acetate, polysulfone, polyamides(nylons), and combinations of them can be mentioned as examples. Among them, combination of polyethylene and polypropylene porous membranes is preferable. Each porous membrane has thickness in a range of about 3 to 40 µm, preferably 5 to 20 µm. At least two layers of membrane, generally two to three layers of membrane are combined to form the liquid blocking layer. The liquid blocking layer has a whole void ratio in a range of about 25 to 90%, preferably about 35 to 90%, and a whole thickness in a range of about 10 to 50 µm, preferably about 10 to 30 µm.

The above mentioned porous membrane is adhered to the aforementioned indicator layer in practical adhesion force. The porous membrane is pasted up to the surface of the indicator layer in wet condition, and dried. Here, wet condition means that the binder of the indicator layer is in a condition of swelling, dispersion or solution by virtue of a residual solvent dissolving the binder or by wetting the dry layer with a dissolving solvent.

Porous membranes composing the liquid blocking layer may be adhered each other in point contact with a physical and/or chemical technique, such as thermo compression bonding or adhesion using a hot melt adhesive etc. Porous membranes may either be sequentially laminated on the indicator layer or be laminated each other prior to adhesion to the indicator layer.

On the liquid blocking layer, a reagent layer is provided. The reagent layer is the layer usually containing a reagent reacting with the ammonia-producing substance to produce ammonia (generally an enzyme or a reagent containing an enzyme), an alkaline buffering agent for efficiently releasing the ammonia produced during the reaction in a form of gaseous ammonia, and a hydrophilic polymer binder having a film-forming facility. Examples of combination of ammonia-producing substance/reagent are urea/urease, creatinine/creatinine deiminase, amino acid/amino acid dehydrogenase, amino acid/amino acid oxidase, amino acid/amino acid dehydratase, amino acid/ammonia lyase, amine/amine oxidase, diamine/amine oxidase, glucose and phosphoamidate/phosphoamidate hexose phosphotransferase, ADP/carbamate kinase and carbamoylphosphate, acid amide/amide hydrolase, nucleobase/deaminase, nucleoside/deaminase, nucleotide/deaminase, guanine/guanase, and the like.

Alkaline buffering agents in the range of pH 7.0 to 10.5, preferably 7.5 to 10.0, are usually usable for the reagent layer. Specific examples of buffering agents are ethylenediaminetetraacetic acid (EDTA), tris(hydroxymethyl)aminomethane (Tris), phosphate buffering agents, N,N-bis(2-hydroxyethyl)glycine (Bicine), Good's buffering agents, such as N-2-hydroxyethylpiperazine-N'-2-hydroxypropane-3-sulfonic acid (Heppso) and N-hydroxyethylpiperazine-N'-ethanesulfonic acid (Hepes) etc., borate buffering agents, and the like.

Examples of the hydrophilic polymer binder having a film-forming facility usable for the reagent layer include gelatin, agarose, polyvinyl alcohol, polyacrylamide, hydroxymethyl cellulose, hydroxyethyl cellulose, polyvinyl pyrrolidone, and the like.

The reagent layer may contain, if necessary, a wetting agent, a binder-crosslinking agent (a curing agent), stabilizer, a heavy metal ion-trapping agent (a complexing agent) in addition to the reagent capable of reacting with the ammonia-producing substance to form ammonia, the alkaline buffering agent and the film-forming hydrophilic polymer binder.

The reagent layer can be formed by preparing a coating solution by mixing the reagent capable of reacting with the ammonia-producing substance to form ammonia, the alkaline buffering agent and optionally other reagents mentioned above with a film-forming hydrophilic binder such as gelatin, applying it on the liquid blocking layer, then drying it.

The reagent capable of reacting with the ammonia-producing substance to form ammonia is used usually in a range of about 0.1 to 50% by weight, preferably about 0.2 to 20% by weight based on the weight of the binder. The alkaline buffering agent is used appropriately in a range of about 0.1 to 60% by weight based on the weight of the binder. Generally the dry thickness of the reagent layer is in a range of about 1 to 40 μm, preferably about 2 to 20 μm.

On the reagent layer, a spreading layer is provided. The spreading layer may be a woven fabric spreading layer disclosed in U.S. Pat. Nos. 4,292,272, 4,783,315, etc. (e.g. plain weaves including broad cloth and poplin), a knitted fabric spreading layer disclosed in EP 0 162 302 A, etc. (e.g. tricot, double tricot or milanese), a spreading layer made of organic polymer fiber pulp-containing paper disclosed in JP 1982-148250 A, a fibrous microporous spreading layer, such as spreading layers formed by coating a fluid dispersion of fibers and a hydrophilic polymer disclosed in JP 1982-125847 A etc., a membrane filter (blushed polymer layer) disclosed in U.S. Pat. No. 3,992,158, a continuous microspaces-containing isotropic porous spreading layers where fine particles, such as polymer particulates are joined in point contact with a hydrophilic polymer binder, a non-fibrous isotropic porous spreading layer, such as a continuous microspaces-containing porous spreading layer where polymer particulates are joined in point contact with a polymer adhesive which does not swell in water (three-dimensional lattice structure layer) disclosed in U.S. Pat. No. 4,258,001 etc., a spreading layer with a good blood cell-separating ability where plural porous layers (for example, two layers including woven or knitted fabric and membrane filter, three layers including woven or knitted fabric, membrane filter, and woven or knitted fabric) are adhered each other to form a laminate using an adhesive laid on their interfaces in discontinuous points or islands (so called halftone dots in printing field) disclosed in U.S. Pat. No. 5,019,347, JP 1987-138756 A, JP 1987-138757 A, EP 0 226 465 A etc.

Woven fabric or knitted fabric used for the spreading layer can be rendered hydrophilic by processing at least one surface of it with physical activation treatment represented by glow discharge or corona discharge disclosed in U.S. Pat. No. 4,783,315, degreasing by washing with water or impregnating with a hydrophilic polymer disclosed in JP 1980-164356 A, JP 1982-066359 A etc., or by sequential processing of an appropriate combination of these treatments, resulting in a increased adhesion force to the layer located on the underside, i.e. near the support. In addition, a polymer-containing aqueous solution or a polymer-containing mixed solution of water and an organic solvent can be coated on the spreading layer to control expansion area or spread of a liquid sample as disclosed in JP 1984-171864 A, JP 1985-222769 A, JP 1985-222770 A etc.

Between the reagent layer and the spreading layer, a color-blocking layer or a light-reflective layer may be provided. The color-blocking layer or the light-reflective layer is a layer composed of white particulates, such as titan dioxide particulates or barium sulfate particulates, etc. almost uniformly dispersed in a hydrophilic polymer binder such as gelatin, having light-blocking property or both light-blocking and light-reflecting properties and a dry thickness in a range of about 2 to 20 μm.

In addition, a known adhesive layer composed of a hydrophilic polymer can be provided on the reagent layer, the color-blocking layer or the light-reflective layer for the purpose of strong adhesion of the spreading layer to form a laminate. The adhesive layer has a dry thickness in the range of about 0.5 μm to 5 μm.

A surfactant may be added to the reagent layer, the color-blocking layer or light-reflecting layer, the adhesive layer, the spreading layer, or the like. A nonionic surfactant may be mentioned as an example. Specific examples of the nonionic surfactant are p-octylphenoxypolyethyoxyethanol, p-nonylphenoxypolyethoxyethanol, polyoxyethylene oleyl ether, polyoxyethylenesorbitanmonolaurate, p-nonylphenoxypolyglycidol, octylglucoside, and the like. By adding the nonionic surfactant to the spreading layer, the spreading action (metering action) for spreading an aqueous liquid sample is improved. By adding the nonionic surfactant to the reagent layer, the color-blocking layer or light-reflecting layer, or the adhesive layer the water in an aqueous liquid sample is easily and substantially uniformly absorbed by the reagent layer during analytical operations, and the liquid contact with the spreading layer becomes rapid and substantially uniform.

The analysis of ammonia or ammonia-producing substance in a liquid sample using the integral multilayer analytical element in accordance with the invention can be conducted according to a following analytical operation sequence; spot a liquid sample, such as whole blood, plasma, serum, urine, etc. on the spreading layer in a range of 3 to 30 μL, preferably 6 to 15 μL; incubate the spotted element at a substantially constant temperature in a range of about 20° C. to 40° C. for a period in a range of 1 to 10 minutes; measure the degree of color change (coloring or discoloration) occurred in the indicator layer by reflection photometry through the transparent support, or visually compare the hue in the indicator layer with a standard hue.

EXAMPLES

Example 1

The following indicator layer was applied in a form of an ethanol solution onto a transparent polyethylene terephthalate (PET) film having a thickness of 180 μm, and dried.

| Indicator Layer | |
|---|---|
| Bromophenol Blue | 110 mg/m$^2$ |
| Polyvinyl ethyl ether | 1.8 g/m$^2$ |
| (Weight average molecular weight: about 40,000) | |
| Sodium hydroxide | 7 mg/m$^2$ |

On the indicator layer, the porous membrane ① shown in the Table 1 was uniformly pressed to provide a liquid-blocking layer. On the liquid-blocking layer, a following reagent layer was applied in a form of a aqueous solution, and dried. On this occasion, the layer of the porous membrane ① was arranged so as to contact the reagent layer.

| Reagent Layer | |
|---|---|
| Hydroxyethyl cellulose | 14 g/m$^2$ |
| (Mean molecular weight: about 40,000) | |
| mean substitution degree of hydroxyethyl group: DS = 1.0 to 1.3 | |
| mean number of moles: MS = 1.8 to 2.5 | |
| Sodium tetraborate | 4 g/m$^2$ |
| (pH of the coating solution: 10.0) | |

Immediately after the above reagent layer was almost uniformly wetted with 0.2% p-nonylphenoxypolyglycidol aqueous solution, a knitted polyester fabric (gauge number: 40) was pressed uniformly to form a laminate.

In addition, polyvinylpyrrolidon was impregnated into the laminate by applying the following ethanol solution for the purpose of improving spreading property, and dried to complete an integral multilayer analytical element for the determination of ammonia.

| | |
|---|---|
| Polyvinylpyrrolidone | 6.8 g/m² |
| (mean molecular weight: about 1,200,000) | |

Example 2

An integral multilayer analytical element for the determination of ammonia was prepared similar to Example 1, except that the membrane ② shown in the Table 1 was used in place of membrane ①.

Comparative Example 1

An integral multilayer analytical element for the determination of ammonia was prepared similar to Example 1, except that the membrane ③ shown in the Table 1 was used in place of membrane ①.

Comparative Example 2

An integral multilayer analytical element for the determination of ammonia was prepared similar to Example 1, except that the membrane ④ shown in the Table 1 was used in place of membrane ①.

On the spreading layer of respective analytical elements, 10 μL of each solution for evaluation test was spotted. After two minutes, optical density (OD) of developed color was measured at 600 nm by the reflection photometry. Then a calibration curve was prepared by plotting the measured optical density versus the ammonia nitrogen concentration. Besides, the above coloring test was repeated ten times as to each analytical element and each solution for evaluation test, and respective optical density was measured. Each measured optical density was converted to ammonia nitrogen concentration by using the above calibration curve, and each coefficient for variation (CV) of the converted values was determined. Results are represented in the Table 2.

TABLE 2

| | | Ammonia Nitrogen Concentration (μ g/dL) | | | |
|---|---|---|---|---|---|
| | | 0 | 50 | 200 | 400 |
| Example 1 | OD: | 0.39 | 0.48 | 0.72 | 0.99 |
| | CV (%): | — | 2.2 | 2.0 | 1.3 |
| Example 2 | OD: | 0.34 | 0.41 | 0.63 | 0.88 |
| | CV (%): | — | 1.74 | 1.24 | 2.26 |
| Comparative Example 1 | OD: | 0.34 | 0.38 | 0.55 | 0.76 |
| | CV (%): | — | 8.1 | 3.5 | 5.2 |
| Comparative Example 2 | OD: | 0.44 | 0.98 | 1.25 | 1.40 |
| | CV (%): | — | 90.3 | 43.2 | 41.7 |

As shown in Table 2, the sensitivity of the analytical elements of Examples 1 and 2 is higher than that of Comparative Examples 1 and 2, and moreover, the measur-

TABLE 1

| Construction of Porous Membranes ① to ④ | | | | |
|---|---|---|---|---|
| | Membrane① | Membrane② | Membrane③ | Membrane④ |
| Layer 1 | | | | |
| thickness (μm) | 9 | 9 | 25 | 25 |
| pore diameter (μm) | 0.1 | 0.1 | 0.1 | 1 to 3 |
| material | polypropylene | polypropylene | polyethylene | polyethylene |
| Layer 2 | | | | |
| thickness (μm) | 7 | 7 | — | — |
| pore diameter (μm) | 1 to 3 | 1 to 3 | — | — |
| material | polyethylene | polyethylene | — | — |
| Layer 3 | | | | |
| thickness (μm) | — | 9 | — | — |
| pore diameter (μm) | — | 0.1 | — | — |
| material | — | polypropylene | — | — |
| Mean Void Ratio | 44 | 40 | 32 | 65 |

Evaluation of Integral Multilayr Analytical Elements for TEH Determination of Ammonia Integral multilayer analytical elements for the determination of ammonia of Examples 1 and 2 or Comparative Examples 3 and 4 above mentioned were evaluated by the following method.

Aqueous ammonium sulfate solutions were prepared so as to contain ammonia nitrogen in concentration of 0, 60, 200 or 400 μg/dL, respectively, to provide solutions for evaluation test.

ing accuracy of them is also improved. Further, the liquid blocking layer of Comparative Example 2 does not work as is expected, and so the solution for evaluation test spotted to the reagent layer reached the indicator layer, resulting in significant deterioration of CV.

According to this invention, a compacter slide can be obtained by using a thinner porous membrane, and so it is stably fabricated since the whole thickness of it corresponds with those of other slides.

The invention claimed is:

1. In an integral multilayer analytical element for the determination of ammonia or an ammonia-producing substance comprising a transparent support, an indicator layer containing an indicator which produces a detectable change by gaseous ammonia, a liquid blocking layer permitting gaseous ammonia to pass therethrough, a reagent layer containing an alkaline buffering agent and optionally a reagent capable of reacting with said ammonia-producing substance to produce ammonia, and a spreading layer, adhesively laminated in this order, the improvement which comprises that said liquid blocking layer is composed of at least two types of porous membrane layers which are impermeable to aqueous liquids, wherein a pore diameter of an uppermost porous membrane of said at least two types of porous membrane layers, which contacts said reagent layer, is smaller than that of a just underlying porous membrane.

2. The integral multilayer analytical element as claimed in claim 1, wherein said at least two porous membrane layers comprise a porous polypropylene membrane and a porous polyethylene membrane.

3. The integral multilayer analytical element as claimed in claim 1, wherein said liquid blocking layer has a total thickness of 10 to 50 µm.

4. The integral multilayer analytical element as claimed in claim 1, wherein said pore diameter in the uppermost membrane is 0.01 to 1 µm and that of the just underlying porous membrane is 0.2 to 20 µm.

5. The integral multilayer analytical element as claimed in claim 1, wherein a ratio of the pore diameter of the uppermost porous membrane to the pore diameter of the just underlying porous membrane is in a range of 0.01 to 0.5.

* * * * *